(12) United States Patent
Preiss et al.

(10) Patent No.: US 9,378,485 B2
(45) Date of Patent: Jun. 28, 2016

(54) SYSTEMS AND METHODS FOR APPLYING GEOLOCATION TO WORKFLOWS USING MOBILE MEDICAL CLIENTS

(75) Inventors: Erik Glenn Preiss, Underhill, VT (US); John Cicilio, Fairfield, VT (US); Ray LaRose, Williston, VT (US); Jacques E. Gilbert, Essex Junction, VT (US); Jessica Bolduc, South Burlington, VT (US); Rick Gouse, Burlington, VT (US); Jeff French, Burlington, VT (US); Rodolfo Chavez, Bensenville, IL (US); Cullen A. Clark, Canaan, NH (US)

(73) Assignee: General Electric Company, Schenectady, NY (US)

( * ) Notice: Subject to any disclaimer, the term of this patent is extended or adjusted under 35 U.S.C. 154(b) by 481 days.

(21) Appl. No.: 12/982,336

(22) Filed: Dec. 30, 2010

(65) Prior Publication Data

US 2012/0173257 A1 Jul. 5, 2012

(51) Int. Cl.
  *G06Q 50/22* (2012.01)
  *G06Q 50/24* (2012.01)
  *G06Q 10/10* (2012.01)
  *G06Q 10/06* (2012.01)

(52) U.S. Cl.
  CPC ............. *G06Q 10/103* (2013.01); *G06Q 10/06* (2013.01); *G06Q 50/22* (2013.01)

(58) Field of Classification Search
  CPC .............................. G06Q 50/22; G06Q 50/24
  See application file for complete search history.

(56) References Cited

U.S. PATENT DOCUMENTS

| | | | | |
|---|---|---|---|---|
| 6,047,259 | A * | 4/2000 | Campbell et al. | 705/3 |
| 7,418,342 | B1 * | 8/2008 | Bell et al. | 701/487 |
| 8,170,960 | B1 * | 5/2012 | Bill | 706/11 |
| 8,180,651 | B2 * | 5/2012 | Molaison | 705/2 |
| 2007/0073477 | A1 * | 3/2007 | Krumm et al. | 701/209 |
| 2008/0120784 | A1 * | 5/2008 | Warner et al. | 5/658 |

OTHER PUBLICATIONS

Riggle, J., "Foursquare in Healthcare?," http://www.livingstonbuzz.com/2010/05/27/foursquare-in-healthcare/, retrieved online May 13, 2011. (6 pages).

* cited by examiner

*Primary Examiner* — Eliza Lam
(74) *Attorney, Agent, or Firm* — Hanley, Flight and Zimmerman, LLC

(57) ABSTRACT

Certain examples provide systems, methods, and apparatus for healthcare configuration based on location information. An example method for location-driven configuration of a healthcare system includes receiving location information from a location device; predicting a destination of the location device based on the location information and one or more parameters associated with the location device; and communicating with a healthcare system at the destination to configure the healthcare system based on the one or more parameters associated with the location device.

13 Claims, 9 Drawing Sheets

SYSTEMS AND METHODS FOR APPLYING GEOLOCATION TO WORKFLOWS USING MOBILE MEDICAL CLIENTS

FIELD

The present invention generally relates to geolocation of a care provider. In particular, the present invention relates to systems, methods, and apparatus for retrieving information and/or configuring equipment based on a location of a care provider.

BACKGROUND

A healthcare environment, such as a hospital or clinic, encompasses a large array of professionals, patients, equipment and computerized information systems. Additionally, a healthcare enterprise, such as a hospital or clinic, may be a multi-building and/or multi-department facility including a plurality of departments, a plurality of information systems, such as healthcare information systems (HIS), radiology information systems (RIS), clinical information systems (CIS), and cardiovascular information systems (CVIS), a plurality of storage systems, such as picture archiving and communication systems (PACS), library information systems (LIS), and electronic medical records (EMR), and a plurality of imaging modalities, such as x-ray systems, computed tomography (CT) systems, ultrasound systems, magnetic resonance imaging (MRI) systems, etc. Information stored may include patient medical histories, imaging data, test results, diagnosis information, management information, and/or scheduling information, for example. The information for a particular information system may be centrally stored or divided at a plurality of locations.

BRIEF SUMMARY

Certain examples provide systems, methods, and apparatus for healthcare configuration based on location information.

Certain examples provide a location-based clinical information retrieval system. The example system includes a memory to include instructions for execution by a processor and a processor to execute instructions stored in the memory. The processor, when executing the instructions, is to provide a location subsystem to receive location information from a location device and predict a destination of the location device based on the location information and one or more parameters associated with the location device. The location subsystem is to communicate with a healthcare subsystem at the destination to configure the healthcare subsystem based on the one or more parameters associated with the location device.

Certain examples provide a tangible computer readable storage medium including executable program instructions which, when executed by a computer processor, cause the computer to implement a location-based clinical information retrieval system. The system includes a location subsystem to receive location information from a location device and predict a destination of the location device based on the location information and one or more parameters associated with the location device. The location subsystem is to communicate with a healthcare system at the destination to configure the healthcare system based on the one or more parameters associated with the location device.

Certain examples provide a method for location-driven configuration of a healthcare system. The method includes receiving location information from a location device; predicting a destination of the location device based on the location information and one or more parameters associated with the location device; and communicating with a healthcare system at the destination to configure the healthcare system based on the one or more parameters associated with the location device.

Figure 1:
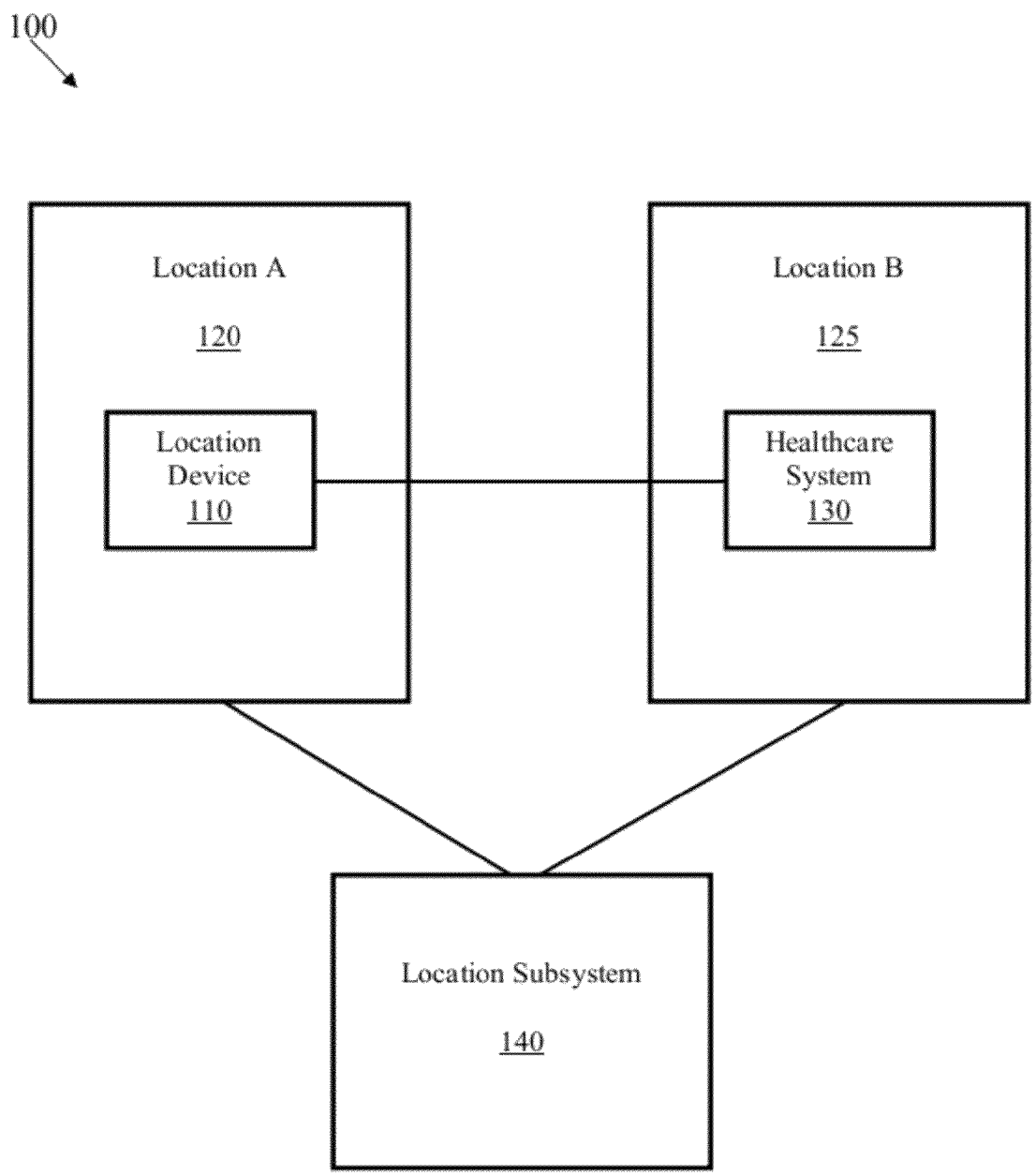
FIG. 1 illustrates an example location system for healthcare applications.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, Blu-ray, etc., storing the software and/or firmware.

Certain examples provide systems, apparatus, and methods to utilize geolocation capabilities of a mobile device to enhance data availability to a clinical provider. For example, a mobile device user has moved from facility A to facility B, and, therefore, default search and/or other parameter in a medical application is set for the proper facility (e.g., facility B). In another example, an attending physician may be walking down a hallway doing rounds, and images, reports and/or data for a next patient can be pre-staged to his/her device before the user walks into the next room having a patient for which he/she is responsible.

From a consumer/patient perspective, certain examples provide automated reminders to patients that have outstanding follow-up tasks if they are in the proximity of a facility that has availability within some tolerance. In certain examples, a patient's calendar can be accessed to help ensure that availability is mutual.

In certain examples, geolocation capability found on mobile device platforms (e.g., iPhone™, Android™, etc.) is leveraged to provide coordinates for a current user of the device to a component that can then apply rules to configure and/or drive behavior of an application. Rules can include setting a default search criteria within the application to match the user's current facility, prefetching data based on the user's current location, launching one or more applications with one or more parameters based on the user's current location, mapping geolocation information from multiple users together, etc.

Certain examples track and/or otherwise identify user location via one or more techniques include geolocation, radiofrequency identification (RFID), Bluetooth wireless tracking, infrared, etc., to eliminate or minimize data entry by a user. In addition to data entry minimization, certain examples may also be used to shift the execution of work in time, so that, rather than forcing a user to wait for information to download to a device, a prediction of which data is needed/wanted next can be made to initiate a download of data and/or launch of application earlier in time.

In certain examples, geolocation is closely related to positioning but can be distinguished from it by a greater emphasis on determining a meaningful location (e.g., a street address) rather than just a set of geographic coordinates. In certain examples, this involves use of radio frequency location systems utilizing, for example, time difference of arrival (TDOA) where greater specificity of location is possible. TDOA systems can utilize mapping displays and/or other graphical information systems, for example. This is in contrast to more traditional radio location technologies, such as direction finding, where a line of bearing to a transmitter is achieved and not the specific location.

In certain examples, using Internet and/or other computer system(s), geolocation can be performed by associating a geographic location with an Internet Protocol (IP) address, media access control (MAC) address, RFID, hardware embedded article/production number, embedded software number (such as UUID, Exif/IPTC/XMP, modern steganography, etc.), invoice, Wi-Fi connection location, device GPS coordinates, and/or other, perhaps self-disclosed, information. Geolocation can be facilitated by automatically looking up an IP address on a WHOIS service and retrieving the registrant's physical address, for example.

IP address geolocation data can include information such as country, region, city, postal/zip code, latitude, longitude and time zone, for example. Deeper data sets can determine other parameters such as domain name, connection speed, Internet service provider (ISP), language, proxy, company name, United States designed market area/metropolitan statistical area (DMA/MSA), North American Industry Classification System (NAICS) codes, and home/business.

Certain examples use a device with geolocation capabilities to track a location of staff (including doctors, nurses, specialists, field engineers, custodians, etc.), patients, and/or equipment. The device(s) provide coordinates of the staff, patients, and equipment to a software component which then applies rules to configure or drive behavior of software applications, for example. For example, the invention can utilize the geolocation capabilities generally found on mobile device platforms (e.g., iPhone™ Android™, etc.) to provide coordinates of a doctor or nurse to a software component which then applies rules to configure or drive behavior of a monitoring device in a patients room or the mobile device itself.

FIG. 1 illustrates an example location system 100 for healthcare applications. The example system 100 includes a location device 110 carried by a user at a location A 120. The device 110 is transitioning to a location B 125 which includes a healthcare system 130. A location subsystem 140 tracks a location of the device 110 and communicates with the healthcare system 130 to load data and/or application(s).

The location device 110 of the example of FIG. 1 can be a cellular phone, pager, global positioning device, tablet computer, laptop computer, and/or other electronic device including location determination capability (e.g., infrared, GPS, RFID, WiFi, cellular triangulation, etc.). The healthcare system 130 can include one or more information and/or modality systems, such as a hospital information system (HIS), radiology information system (RIS), clinical information system (CIS), and cardiovascular information system (CVIS), picture archiving and communication system (PACS), library information system (LIS), electronic medical record (EMR), x-ray system, computed tomography (CT) system, ultrasound system, magnetic resonance imaging (MRI) system, and/or other information system, storage, imaging modality, etc.

For example, a care provider carries a mobile device 110 or other device with geolocation capability. The geolocation device 110 sends occasional location updates to the location subsystem 140 tracking location of personnel in a healthcare enterprise. The location subsystem 140 is aware of the types of care services that the care provider is both certified and licensed to perform for the given location (e.g., care providers are both licensed and certified state by state). The location subsystem 140 provides a notification information packet to service locations (e.g., hospitals, clinics, first responders, etc.) regarding the licensed and certified capabilities of the care/service provider.

For example, the location subsystem 140 of the example of FIG. 1 can then send updates to an Electronic Medical Record (EMR) system and/or other system 130 to coordinate fetching for a set of patients who may be treated by the care provider (e.g., whose location was identified and sent to a tracking application). Information fetched for the patient(s) is then staged at appropriate viewing and/or diagnostic equipment at location B 125 to facilitate accurate and timely care for the patient, for example.

When a match is made between the provider and the patient service to be rendered, appropriate information, matched to the capabilities of the mobile device of the provider, is forwarded to the provider's device 110 to allow for knowledge and mental preparation for the situation at hand.

In certain examples, in addition to pre-fetching information, the information is provided to Quality of Care (QoC) system(s)/application(s) which evaluate, based on existing data sets, the most cost effective and effective care that has been provided for patients with similar dispositions.

Coordinated identification of provider and information retrieval can help provide accurate and timely information to facilitate high quality data driven care for a patient, for example. For example, information coordination can be useful for coordination of emergency services (e.g., a natural disaster with a mix of care providers and patients who are possibly from disparate locations). Additionally, coordination can be used for customization of interfaces for any particular person wearing the geolocation device 110, for example.

Once the medical records and decision support data have been fetched to a location 125, the information can be integrated with decision support to provide a set of probabilistic scenarios for the care giver to analyze for the patient. As the care giver then moves within a facility, specific equipment is preloaded and configured, per the care givers preferred settings, with the information and recommendations for the patient, for example.

Thus, timely and accurate staging of information and applications can be provide which takes captured location information (e.g., user coordinates in space) and applies the location information to facilitate accurate and timely provision and configuration of medical device(s)/system(s). In addition to data entry minimization, certain examples can be used to shift execution of time and/or data intensive work ahead in time. Thus, rather than forcing a care provider to wait for information to download to a device or for an application to load, a prediction of next likely data needed by a user for a patient can be made and a fetching of that information/loading of application(s)/configuration of equipment can be initiated earlier in time, thereby providing those few extra minutes which are often so crucial in an emergency care situation, for example.

For example, a doctor making rounds can be detected, and patients in a hospital wing associated with that doctor can have their information prefetched for review as the doctor enters their rooms on his or her rounds. As another example, an emergent patient can have his or her information prefetched for a nearest doctor approaching the patient's location for assistance.

Certain examples utilize computational and bandwidth capabilities available on a network in advance of a time of first use by the care provider. Certain example allow for an automatic "think ahead" for the care provider, thereby allowing for a sort of enhanced cognitive capability, thinking, as it may be, to prepare the medical technical space.

Certain examples provide a differentiator for care providers, allowing them to take advantage of available computation and information, and thereby providing an enhanced cognitive capability at the point and time of care. Additionally, certain examples can apply to a variety of workflows.

Figure 2:
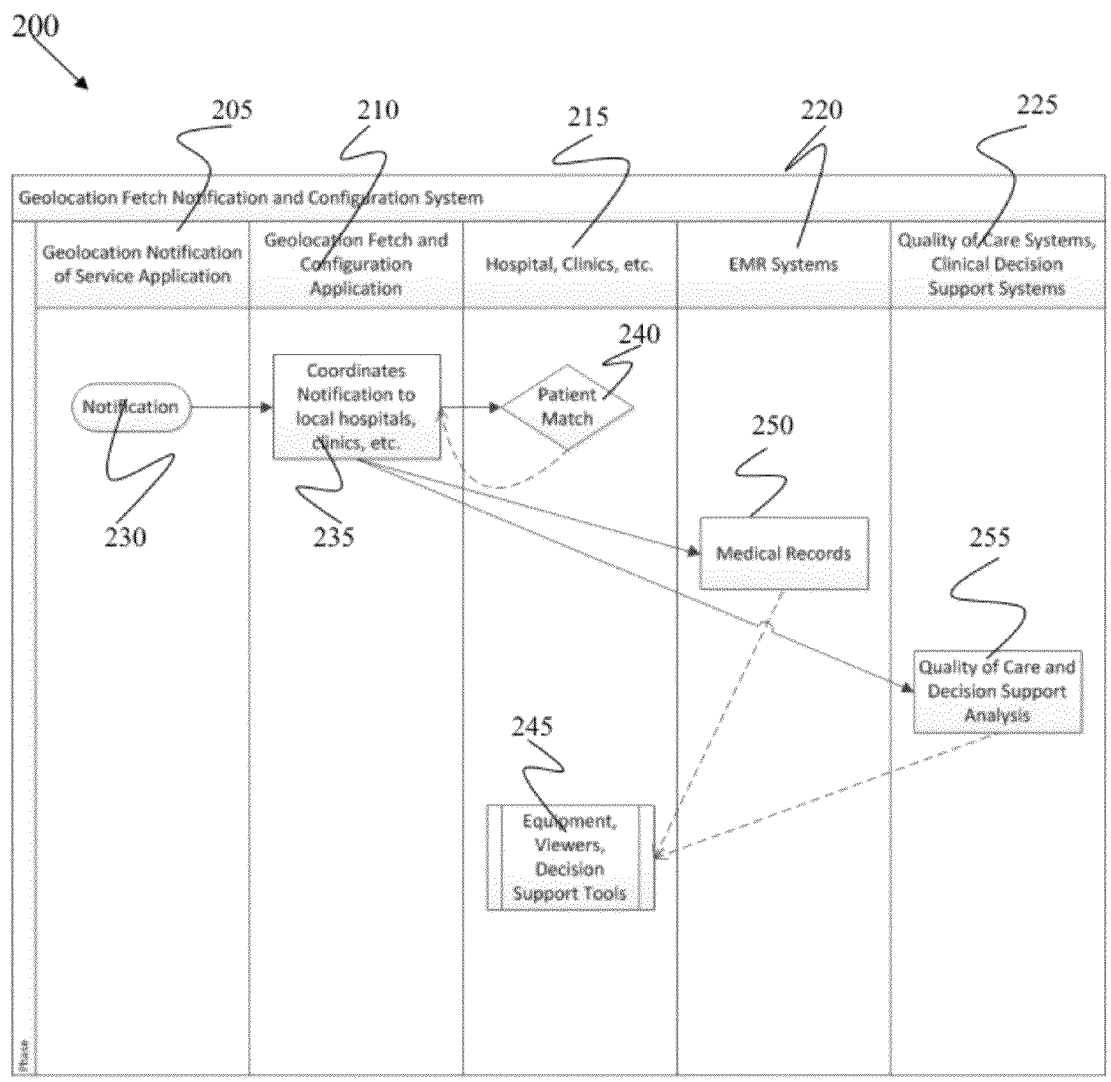
FIG. 2 illustrates an example geolocation fetch notification and configuration system.

FIG. 2 illustrates an example geolocation fetch notification and configuration system 200. The system 200 includes a geolocation notification of service application 205, a geolocation fetch and configuration application 210, a healthcare facility 215, an electronic medical record (EMR) system 220, and one or more support systems 225 (including a quality of care system, clinical decision support system, etc.). As shown in the example of FIG. 2, the notification of service application 205 generates a notification 230 of a user's location and transmits the location to the fetch and configuration application 210.

The fetch and configuration application 210 generates a coordinate notification 235 for a healthcare facility 215, such as a hospital, clinic, etc. The coordinate notification 235 can also be sent to the EMR 220 and/or support system(s) 225, for example. The healthcare facility 215 uses the coordinate notification information 235 to match the user with one or more patients 240 at the facility 215. The EMR 220 uses the coordinate notification information 235 to identify and retrieve associated medical record(s) 250. The support system(s) 225 use the coordinate notification information 235 to generate quality of care and/or decision support analysis 255, for example. In certain examples, the medical record(s) 250 and/or analysis 255 can be provided to the facility 215 to arrange and/or configure equipment, viewer(s), decision support tool(s), etc. 245 at the healthcare facility 215.

Figure 3:
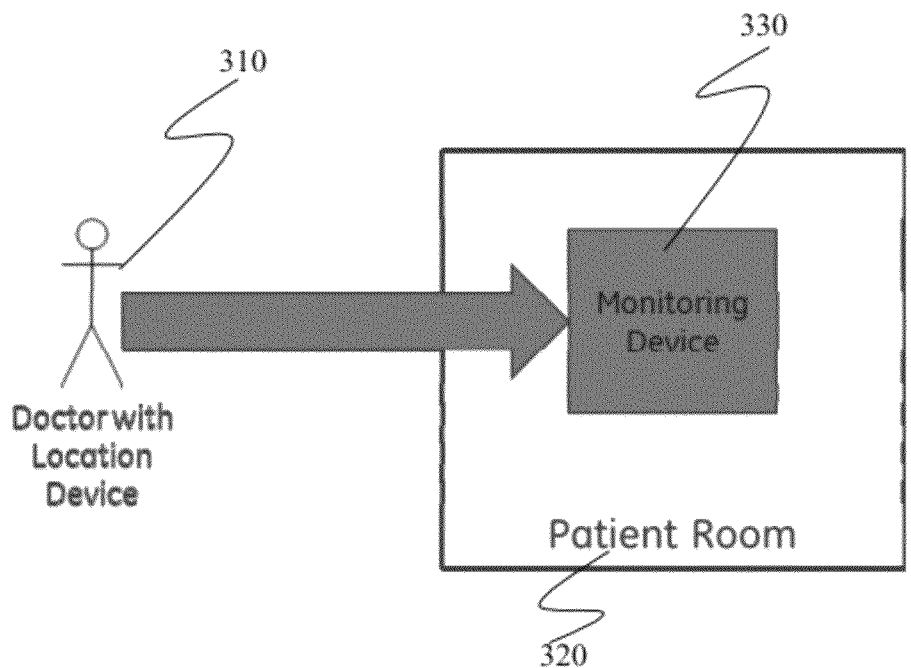
FIGS. 3-9 illustrate example systems involving geolocation devices, users, and locations.

As illustrated in the example of FIG. 3, a member of hospital personnel 310 (e.g., a doctor) enters a patient room 320. The doctor 310 carries a geolocational device 330. The geolocation device 330 can use any of various technologies, including WiFi, Bluetooth, RFID, GPS, and/or other mechanism to calculate location and provide location information to a location tracking software. The software can then, as the doctor 310 approaches a patient's room 320, update equipment in the room 320 to launch appropriate application(s), preload applicable patient(s), and configure setting(s) based on one or more rules, preferences, setting, etc., associated with the doctor 310, patient, room 320, etc. For example, if the doctor 310 is a radiologist, an imaging application is loaded along with recent imaging exam(s) for the given patient. For example, if the doctor 310 is a surgeon, an application detailing the patient's upcoming and/or recent surgery is loaded.

Figure 4:
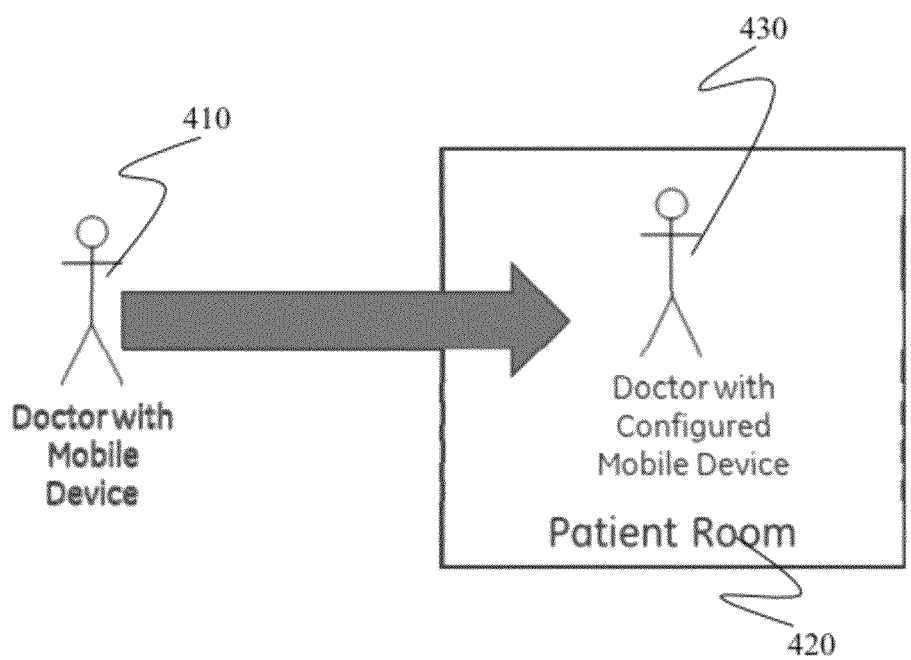

In FIG. 4, the actor 410 may be the same as in FIG. 3, for example. A difference between FIG. 3 and FIG. 4 is that when the doctor 410 in the example of FIG. 4 enters a given room 420, the mobile device(s) in the doctor's possession are configured 430, with applications loaded and information fetched. These mobile devices 430 can include devices such as a tablet computer, an iPad™, an iPhone™, a BlackBerry™, an Android-based phone, etc. Other mobile devices that have an ability to potentially display health information may also be applicable.

Figure 5:
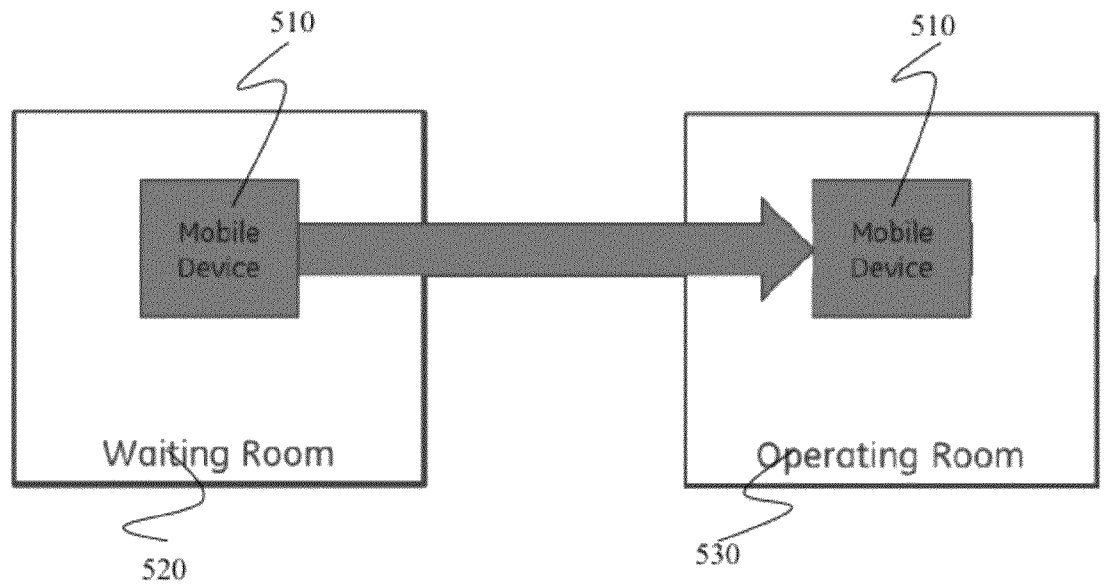

In FIG. 5, geolocational information finding(s) are not tied to a particular person. Instead, location information is attached to a particular device 510. The device 510 can then be moved throughout the facility (e.g., hospital), and be configured appropriately. For example, the device 510 can be a computer on a movable cart. The computer loads and configures different software when moved from a waiting room 520 to an emergency room or operating room 530, for example.

Figure 6:
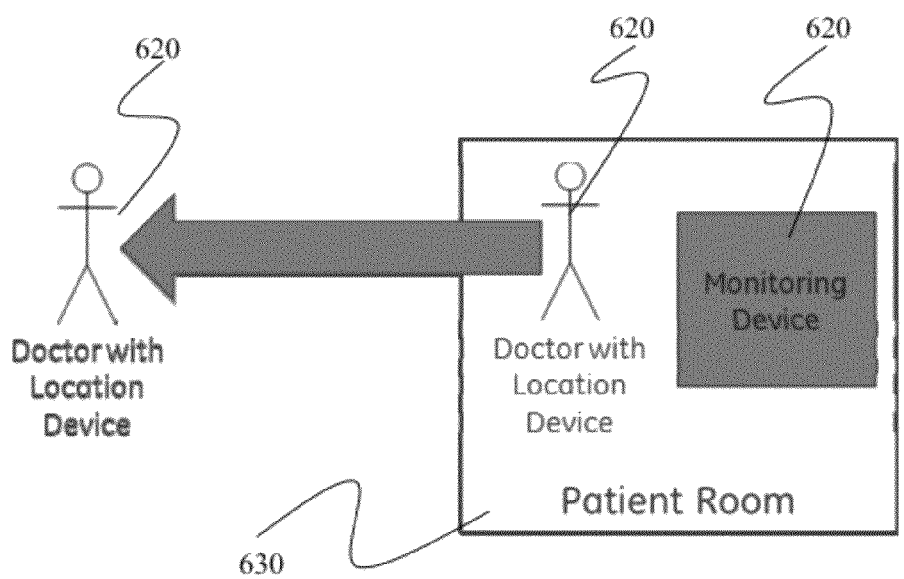

In FIG. 6, a geolocation device 610 in a doctor's 620 possession informs a location service that the doctor 620 is leaving a patient's room 630. The device 610 in the patient room 630 then returns to its default application setting. Sensitive information and applications meant only for the doctor's eyes is hidden, for example.

Figure 7:
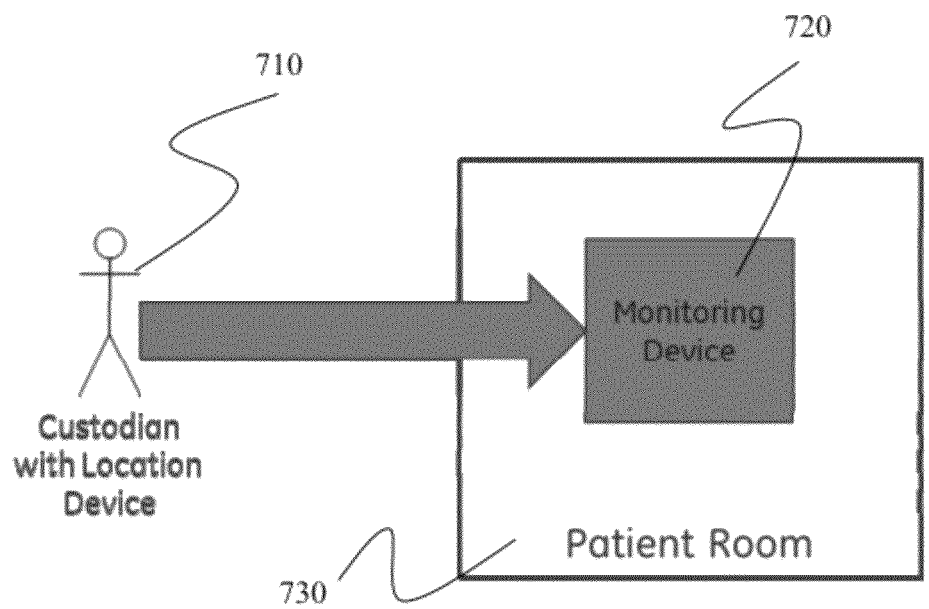

In FIG. 7, a custodian or non-medical staff 710 enters a patient room 730 with a geolocation device 720. Application(s) and/or sensitive information left open/available on the device 720 in the room 730 is locked and hidden from the custodian 710. For example, on the monitoring device 720, a patient's sensitive information such as name, date of birth, height, weight, etc., is hidden, but vital signs remain visible.

Figure 8:
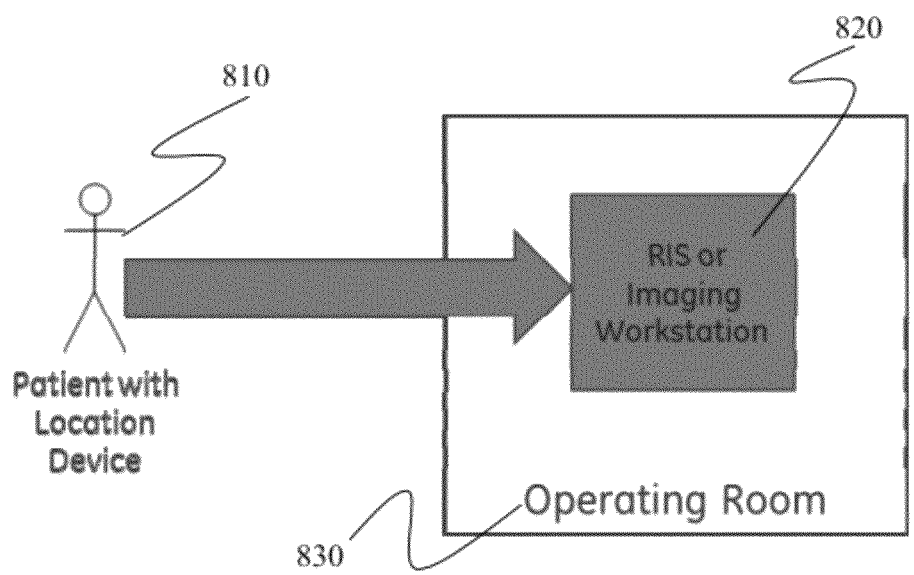

In FIG. 8, a patient with a geolocation device 810 enters a room 830 including a computer workstation 820 (e.g., a RIS and/or imaging workstation). The geolocation device informs a location service, and the location service preloads the workstation 820 in the, for example, operating room 830 with the patient's information and appropriate application(s) for surgery. For example, the workstation 820 prepares a RIS application to display information about the procedure to be performed on the patient 810 along with all of the patient's information such as name, date of birth, height, weight, etc. If there are images associated with the surgery, the imaging workstation 820 is also preloaded with the image(s).

Figure 9:
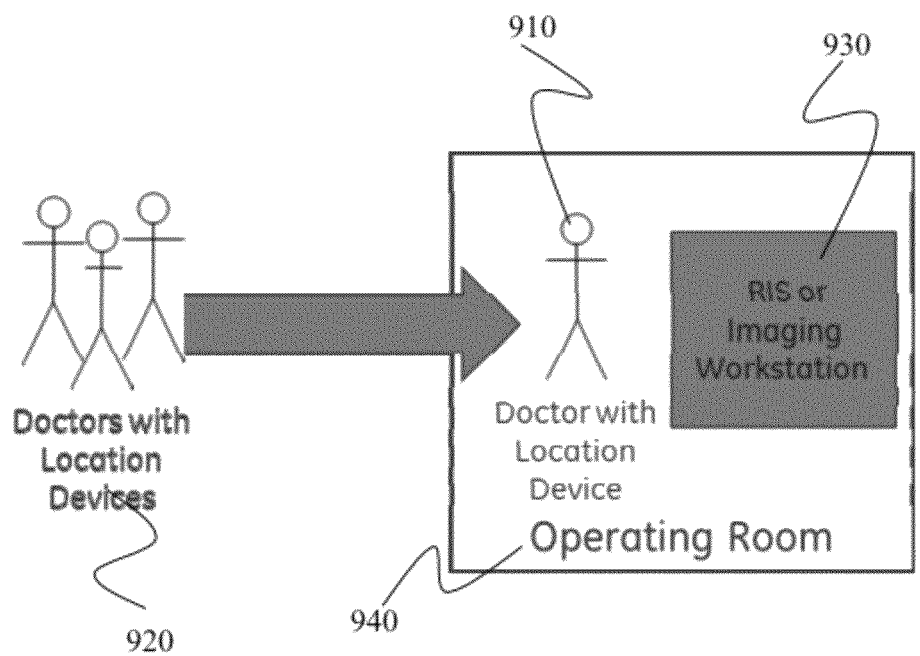

In FIG. 9, a doctor 910 is in a room 940 using a workstation 930 that has been previously configured for her usage, with correct patient data and application(s) loaded. One or more additional doctors and/or medical staff 920 enter the room 940 (e.g., an operating room), each with a geolocation device. A location service configures the workstation 930 in the room 940 with a collaboration application that allows the doctors 910, 920 to view patient information for an upcoming or ongoing surgery and/or other procedure in a more collaborative way.

Figure 10:
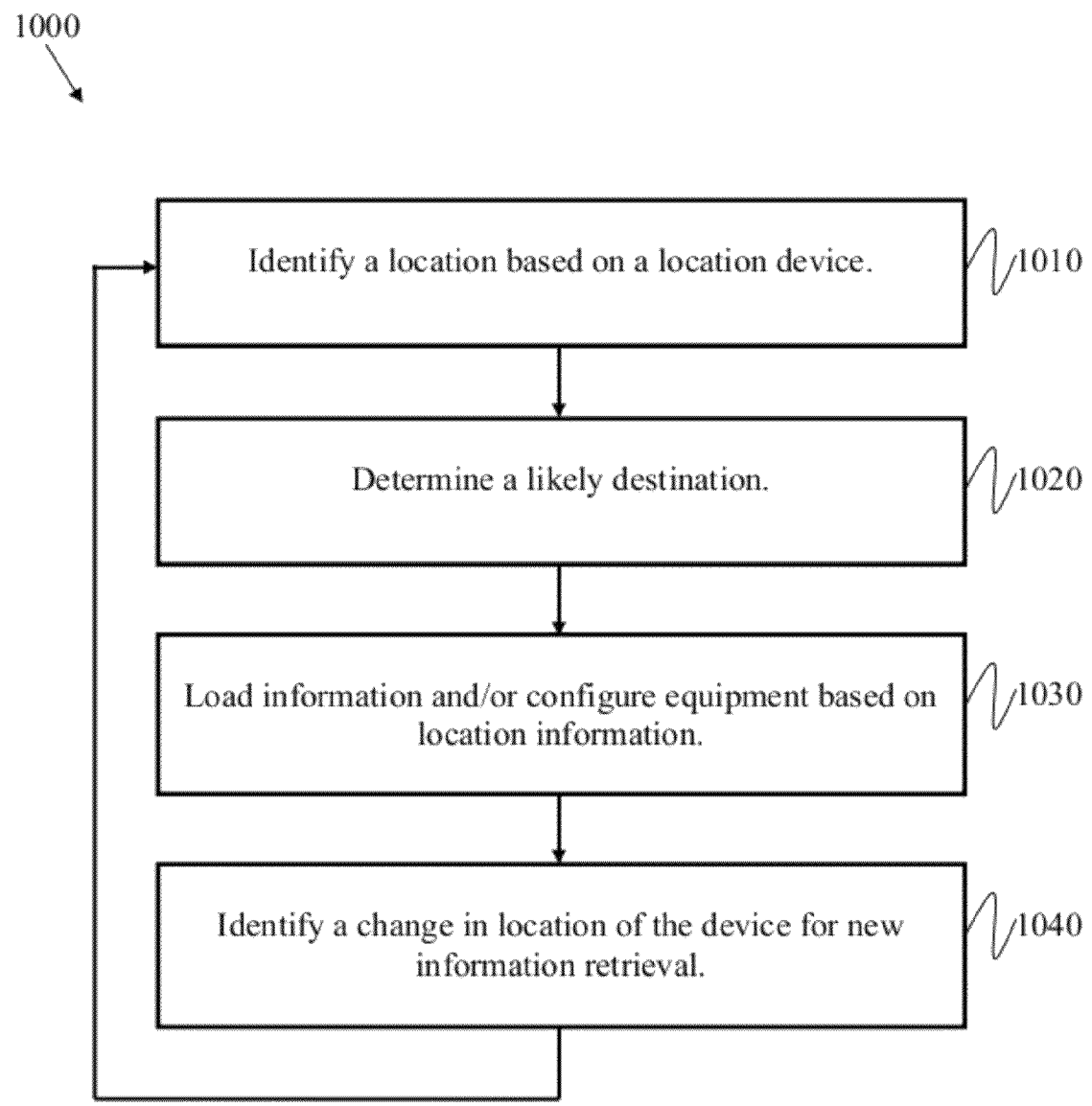
FIG. 10 depicts a flow diagram for an example method for locating a care provider and prefetching related information.

FIG. 10 is a flow diagram representative of example machine readable instructions that can be executed to implement the example systems shown in FIGS. 1-9 and/or portions of one or more of those systems. The example process(es) of FIG. 10 can be performed using a processor, a controller and/or any other suitable processing device. For example, the example process(es) of FIG. 10 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example process(es) of FIG. 10 can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example process(es) of FIG. 10 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example process(es) of FIG. 10 can be implemented manually or as any combination(s) of any of the foregoing techniques, for example, any combination of firmware, software, discrete logic and/or hardware. Further, although the example process(es) of FIG. 10 is described with reference to the flow diagram of FIG. 10, other methods of implementing the process(es) of FIG. 10 can be employed. For example, the order of execution of the blocks can be changed, and/or some of the blocks described can be changed, eliminated, sub-divided, or combined. Additionally, any or all of the example process(es) of FIG. 10 can be performed sequentially and/or in parallel by, for example, separate processing threads, processors, devices, discrete logic, circuits, etc.

FIG. 10 illustrates a flow diagram for a method 1000 for locating a care provider and prefetching related information. At block 1010, a location of a care provider is identified based on a location device. For example, the care provider may be carried a smartphone and/or other electronic device capability of sending and/or receiving a signal indicative of a location within a coordinate system. Alternatively or in addition, equipment (e.g., a portable ultrasound cart and/or other imaging and/or information system) can include a location device and be trackable by a location system, such as the location subsystem 140 of FIG. 1.

At block 1020, a likely destination for the holder of the location device is determined. For example, a patient associated with and/or in need of a care provider and/or equipment carrying the location device can be identified, such as via the example location subsystem 140. At block 1030, information associated with the patient and/or the bearer of the location device can be used to load information and/or configure equipment for the patient. For example, patient identification and care provider identification can be used to load a patient's record and/or a doctor's notes in the patient's room. As another example, patient identification and status information can be used to begin configuration of an x-ray scanner to image the patient. Alternatively or in addition, the location device (e.g., the example location device 110) can be configured with information and/or application(s) based on the patient, location, provider, and/or other criterion. In certain examples, decision support system(s) can also provide information to support a provider based on location-based information.

At block 1040, based on a further change in location, information is retrieved and/or equipment is configured based on a new location of the device. For example, as a tracked care provider and/or tracked equipments moves from one patient room to another patient room, different information and/or application(s) are loaded for use in the new location.

Figure 11:
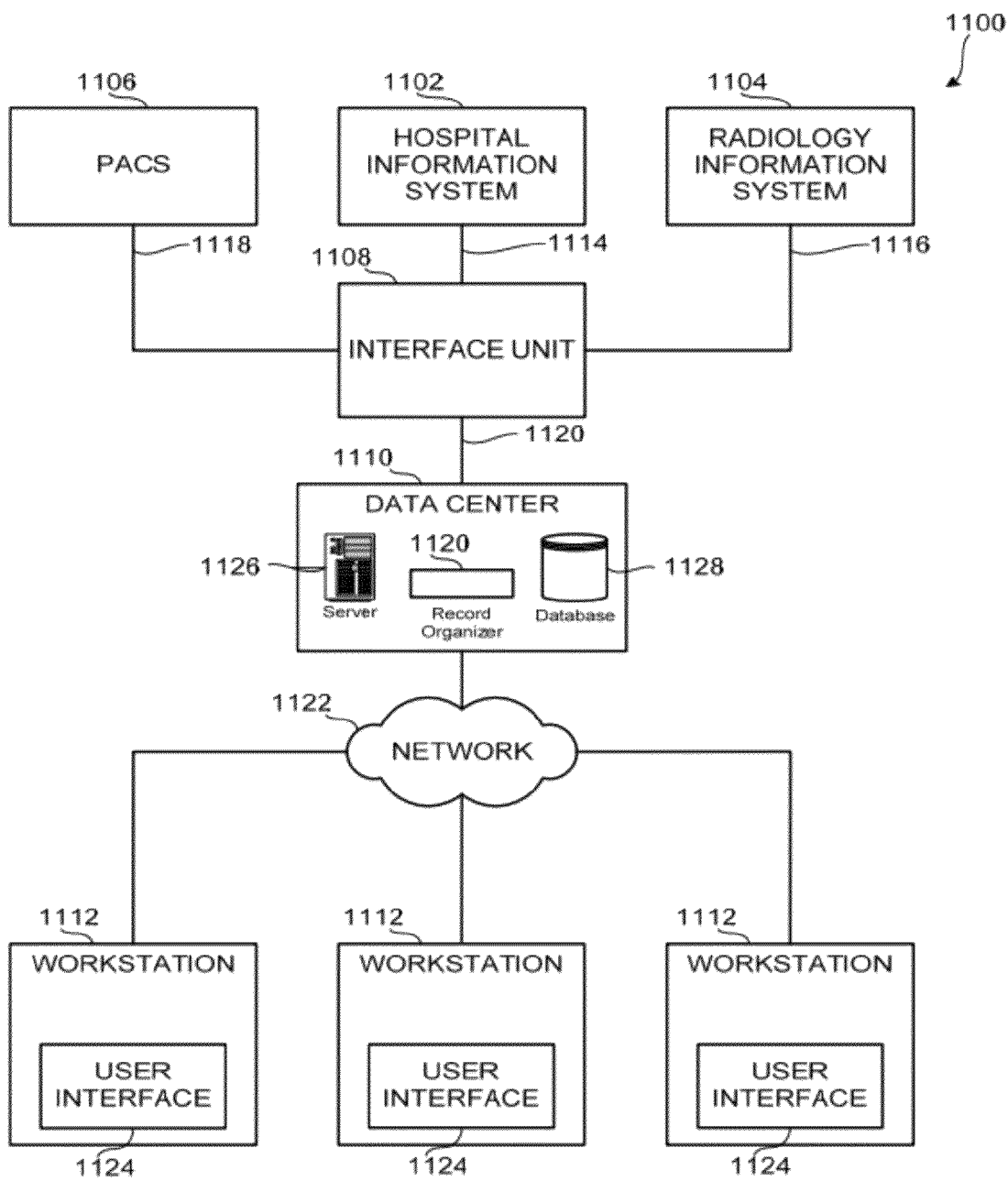
FIG. 11 shows a block diagram of an example clinical information system capable of implementing the example methods and systems described herein.

FIG. 11 shows a block diagram of an example clinical information system 1100 capable of implementing the example methods and systems described herein. The example clinical information system 1100 includes a hospital information system (HIS) 1102, a radiology information system (RIS) 1104, a picture archiving and communication system (PACS) 1106, an interface unit 1108, a data center 1110, and a plurality of workstations 1112. In the illustrated example, the HIS 1102, the RIS 1104, and the PACS 1106 are housed in a healthcare facility and locally archived. However, in other implementations, the HIS 1102, the RIS 1104, and/or the PACS 1106 can be housed one or more other suitable locations. In certain implementations, one or more of the PACS 1106, RIS 1104, HIS 1102, etc., can be implemented remotely via a thin client and/or downloadable software solution. Furthermore, one or more components of the clinical information system 1100 can be combined and/or implemented together. For example, the RIS 1104 and/or the PACS 1106 can be integrated with the HIS 1102; the PACS 1106 can be integrated with the RIS 1104; and/or the three example information systems 1102, 1104, and/or 1106 can be integrated together. In other example implementations, the clinical information system 1100 includes a subset of the illustrated information systems 1102, 1104, and/or 1106. For example, the clinical information system 1100 can include only one or two of the HIS 1102, the RIS 1104, and/or the PACS 1106. Information (e.g., scheduling, test results, observations, diagnosis, etc.) can be entered into the HIS 1102, the RIS 1104, and/or the PACS 1106 by healthcare practitioners (e.g., radiologists, physicians, and/or technicians) before and/or after patient examination.

The HIS 1102 stores medical information such as clinical reports, patient information, and/or administrative information received from, for example, personnel at a hospital, clinic, and/or a physician's office. The RIS 11104 stores information such as, for example, radiology reports, messages, warnings, alerts, patient scheduling information, patient demographic data, patient tracking information, and/or physician and patient status monitors. Additionally, the RIS 1104 enables exam order entry (e.g., ordering an x-ray of a patient) and image and film tracking (e.g., tracking identities of one or more people that have checked out a film). In some examples, information in the RIS 1104 is formatted according to the HL-7 (Health Level Seven) clinical communication protocol.

The PACS 1106 stores medical images (e.g., x-rays, scans, three-dimensional renderings, etc.) as, for example, digital images in a database or registry. In some examples, the medical images are stored in the PACS 1106 using the Digital Imaging and Communications in Medicine ("DICOM") format. Images are stored in the PACS 306 by healthcare practitioners (e.g., imaging technicians, physicians, radiologists) after a medical imaging of a patient and/or are automatically transmitted from medical imaging devices to the PACS 1106 for storage. In some examples, the PACS 1106 can also include a display device and/or viewing workstation to enable a healthcare practitioner to communicate with the PACS 1106.

The interface unit 1108 includes a hospital information system interface connection 1114, a radiology information system interface connection 1116, a PACS interface connection 1118, and a data center interface connection 1120. The interface unit 1108 facilities communication among the HIS 1102, the RIS 1104, the PACS 1106, and/or the data center 1110. The interface connections 1114, 1116, 1118, and 1120 can be implemented by, for example, a Wide Area Network ("WAN") such as a private network or the Internet. Accordingly, the interface unit 1108 includes one or more communication components such as, for example, an Ethernet device, an asynchronous transfer mode ("ATM") device, an 802.11 device, a DSL modem, a cable modem, a cellular modem, etc. In turn, the data center 1110 communicates with the plurality of workstations 1112, via a network 1122, implemented at a plurality of locations (e.g., a hospital, clinic, doctor's office, other medical office, or terminal, etc.). The network 1122 is implemented by, for example, the Internet, an intranet, a private network, a wired or wireless Local Area Network, and/or a wired or wireless Wide Area Network. In some examples, the interface unit 1108 also includes a broker (e.g., a Mitra Imaging's PACS Broker) to allow medical information and medical images to be transmitted together and stored together.

In operation, the interface unit 1108 receives images, medical reports, administrative information, and/or other clinical information from the information systems 1102, 1104, 1106 via the interface connections 1114, 1116, 1118. If necessary (e.g., when different formats of the received information are incompatible), the interface unit 1108 translates or reformats (e.g., into Structured Query Language ("SQL") or standard text) the medical information, such as medical reports, to be properly stored at the data center 1110. The reformatted medical information can be transmitted using a transmission protocol to enable different medical information to share common identification elements, such as a patient name or social security number. Next, the interface unit 1108 transmits the medical information to the data center 1110 via the data center interface connection 1120. Finally, medical information is stored in the data center 1110 in, for example, the DICOM format, which enables medical images and corresponding medical information to be transmitted and stored together.

The medical information is later viewable and easily retrievable at one or more of the workstations 1112 (e.g., by their common identification element, such as a patient name or record number). The workstations 1112 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 312 receive commands and/or other input from a user via, for example, a keyboard, mouse, track ball, microphone, etc. As shown in FIG. 11, the workstations 1112 are connected to the network 1122 and, thus, can communicate with each other, the data center 1110, and/or any other device coupled to the network 1122. The workstations 1112 are capable of implementing a user interface 1124 to enable a healthcare practitioner to interact with the clinical information system 1100. For example, in response to a request from a physician, the user interface 1124 presents a patient medical history. Additionally, the user interface 1124 includes one or more options related to the example methods and apparatus described herein to organize such a medical history using classification and severity parameters.

The example data center 1110 of FIG. 11 is an archive to store information such as, for example, images, data, medical reports, and/or, more generally, patient medical records. In addition, the data center 1110 can also serve as a central conduit to information located at other sources such as, for example, local archives, hospital information systems/radiology information systems (e.g., the HIS 1102 and/or the RIS 1104), or medical imaging/storage systems (e.g., the PACS 1106 and/or connected imaging modalities). That is, the data center 1110 can store links or indicators (e.g., identification numbers, patient names, or record numbers) to information. In the illustrated example, the data center 1110 is managed by an application server provider ("ASP") and is located in a centralized location that can be accessed by a plurality of systems and facilities (e.g., hospitals, clinics, doctor's offices, other medical offices, and/or terminals). In some examples, the data center 1110 can be spatially distant from the HIS 1102, the RIS 1104, and/or the PACS 1106 (e.g., at General Electric® headquarters).

The example data center 1110 of FIG. 11 includes a server 1126, a database 1128, and a record organizer 1130. The server 1126 receives, processes, and conveys information to and from the components of the clinical information system 1100. The database 1128 stores the medical information described herein and provides access thereto. The example record organizer 1130 of FIG. 11 manages patient medical histories, for example. The record organizer 1130 can also assist in procedure scheduling, for example.

Figure 12:
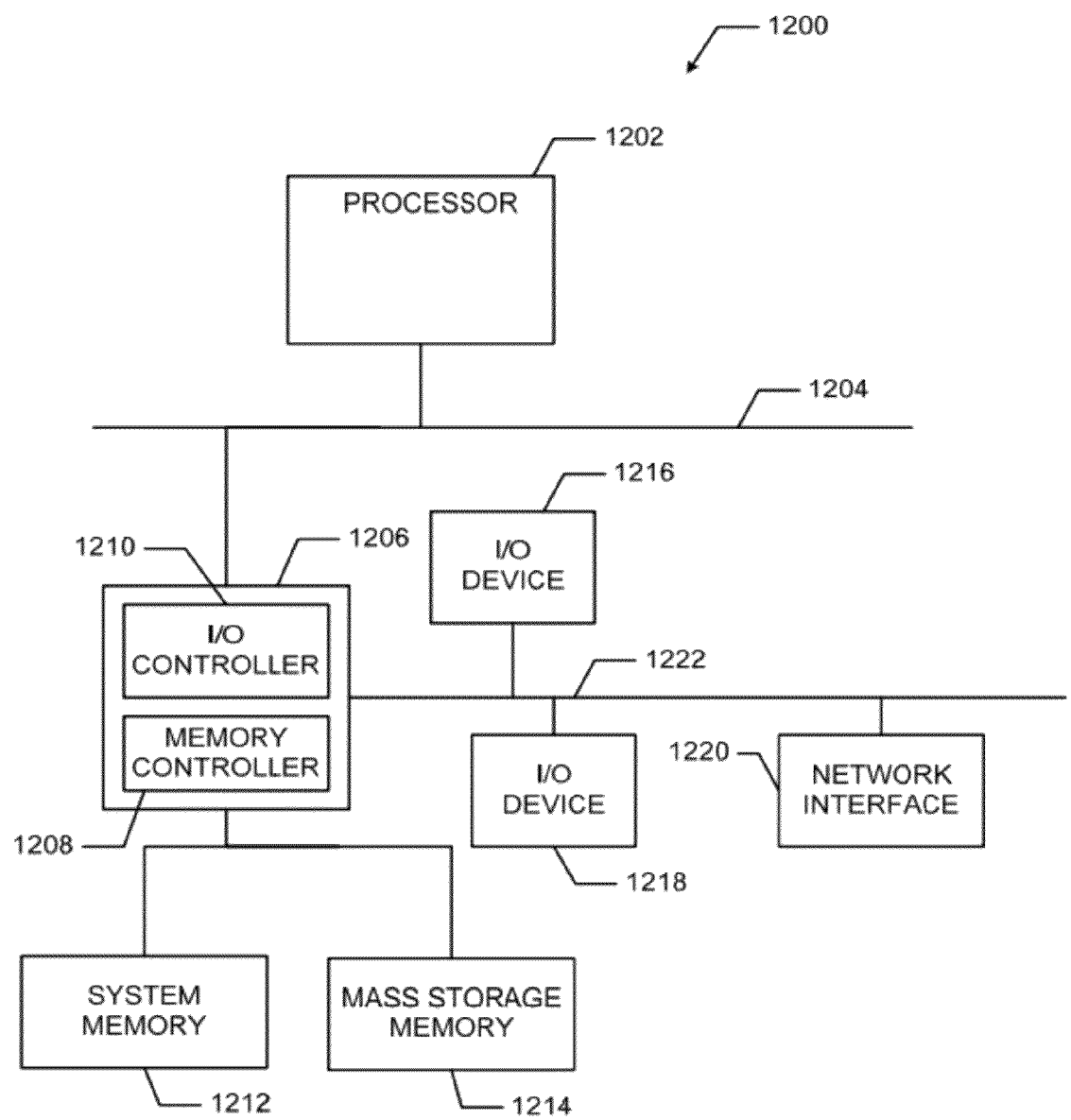
FIG. 12 is a block diagram of an example processor system that may be used to implement systems, apparatus, and methods described herein.

FIG. 12 is a block diagram of an example processor system 1210 that can be used to implement systems, apparatus, and methods described herein. As shown in FIG. 12, the processor system 1210 includes a processor 1212 that is coupled to an interconnection bus 1214. The processor 1212 can be any suitable processor, processing unit, or microprocessor, for example. Although not shown in FIG. 12, the system 1210 can be a multi-processor system and, thus, can include one or more additional processors that are identical or similar to the processor 1212 and that are communicatively coupled to the interconnection bus 1214. For example, "cloud" and/or "grid" based computing can be employed for three dimensional processing using Euclidian vectors and linear algebra, as described above. In certain examples, a Bayesian algorithm can be used in an evolving model combining multiple executions of multiple algorithms. As certain mappings are resolved, a probability associated with other remaining mappings changes.

The processor 1212 of FIG. 12 is coupled to a chipset 1218, which includes a memory controller 1220 and an input/output ("I/O") controller 1222. As is well known, a chipset typically provides I/O and memory management functions as well as a plurality of general purpose and/or special purpose registers, timers, etc. that are accessible or used by one or more processors coupled to the chipset 1218. The memory controller 1220 performs functions that enable the processor 1212 (or processors if there are multiple processors) to access a system memory 1224 and a mass storage memory 1225.

The system memory 1224 can include any desired type of volatile and/or non-volatile memory such as, for example, static random access memory (SRAM), dynamic random access memory (DRAM), flash memory, read-only memory (ROM), etc. The mass storage memory 1225 can include any desired type of mass storage device including hard disk drives, optical drives, tape storage devices, etc.

The I/O controller 1222 performs functions that enable the processor 1212 to communicate with peripheral input/output ("I/O") devices 1226 and 1228 and a network interface 1230 via an I/O bus 1232. The I/O devices 1226 and 1228 can be any desired type of I/O device such as, for example, a keyboard, a video display or monitor, a mouse, etc. The network interface 1230 can be, for example, an Ethernet device, an asynchronous transfer mode ("ATM") device, an 802.11 device, a DSL modem, a cable modem, a cellular modem, etc., that enables the processor system 1210 to communicate with another processor system.

While the memory controller 1220 and the I/O controller 1222 are depicted in FIG. 12 as separate blocks within the chipset 1218, the functions performed by these blocks can be integrated within a single semiconductor circuit or can be implemented using two or more separate integrated circuits.

Certain examples provide systems, apparatus, and methods for automated subscription, scheduling, and review of an MDT process for a patient. Certain examples utilize a subscription-based model to keep an administrator and/or other user (e.g., attending physician) informed and to facilitate the MDT review. Certain examples facilitate an automated MDT workflow triggered by physician identification of a patient as warranting an MDT review.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 1210 of FIG. 12). When any of the appended claims are read to cover a purely software and/or firmware implementation, at least one of the components is hereby expressly defined to include a tangible medium such as a memory, DVD, CD, Blu-ray disc, etc. storing the software and/or firmware.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media can be any available media that can be accessed by a general purpose or special purpose computer or other machine with a processor. By way of example, such computer-readable media can include RAM, ROM, PROM, EPROM, EEPROM, Flash, CD-ROM, DVD, Blu-ray or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

While the invention has been described with reference to certain embodiments, it will be understood by those skilled in the art that various changes can be made and equivalents can be substituted without departing from the scope of the invention. In addition, many modifications can be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A location-based clinical information retrieval system comprising:
 a mobile location device including a first processor and a first memory associated with and carried by a care provider to generate location information associated with the care provider;
 a location subsystem including a second memory storing instructions and a second processor to execute the instructions stored in the memory to receive the location information from the mobile location device and to predict a destination of the care provider based on the location information and one or more parameters associated with the mobile location device, the location subsystem to communicate an information packet to an imaging workstation associated with the destination of the care provider, the information packet including settings to configure the imaging workstation at the destination based on the one or more parameters associated with the mobile location device, the one or more parameters including an identification of the care provider associated with the mobile location device,
 wherein the location subsystem is to match a patient at the predicted destination with the care provider based on a comparison of the predicted destination to a list of patients at or near the predicted destination for whom the care provider is eligible to provide care to identify the patient, the location subsystem to retrieve a patient information including an a imaging exam for the patient, based on the identification of the patient and one or more patient services associated with the eligibility of the care provider to provide care for the patient, and to transmit the patient information including the imaging exam to pre-load the imaging workstation at the predicted destination in advance of the arrival of the location device, wherein as the mobile location device is moved from one destination to another, the location subsystem pre-loads different information packets to the imaging workstations at each destination.

2. The system of claim 1, wherein the location subsystem is to communicate with decision support regarding the destination.

3. The system of claim 1, wherein the imaging workstation is one of a Computed Tomography (CT) system, an X-ray system, an ultrasound system, and an MR imaging system.

4. The system of claim 1, wherein the healthcare equipment provides information to the mobile location device based on a communication from the location subsystem.

5. The system of claim 1, wherein the location subsystem is to arrange a review of a plurality of patients based on location information from the location device.

6. A non-transitory, tangible computer readable storage medium including executable program instructions which, when executed by a first computer processor, causes the first computer processor in combination with a mobile location device to implement a location-based clinical information retrieval system including a location subsystem, the mobile location device including a second processor and a second memory associated with and carried by a care provider to generate location information associated with the care provider, the program instructions to instruct the first computer processor to perform:
   receiving a location information from the mobile location device;
   predicting a predicted destination of the care provider based on the location information and one or more parameters associated with the mobile location device;
   matching a patient at the predicted destination with the care provider based on a comparison of the predicted destination to a list of patients at or near the predicted destination for whom the care provider is eligible to provide care to;
   retrieving a patient information for the patient based on the identification of the patient and one or more patient services associated with the eligibility of the care provider to provide care for the patient and communicating an information packet to an imaging workstation located at the predicted destination of the care provider, the information packet including the patient information and settings to configure the imaging workstation based on the one or more parameters associated with the mobile location device, the one or more parameters including an identification of the care provider associated with the mobile location device,
   wherein as the mobile location device moves from one destination to another, different information packets are pre-loaded to the imaging workstations at each destination.

7. The storage medium of claim 6, wherein the location subsystem is to communicate with decision support regarding the predicted destination.

8. The storage medium of claim 6, wherein the location subsystem determines a geolocation of the mobile location device.

9. The storage medium of claim 6, wherein the imaging workstation is one of a Computed Tomography (CT) system, an X-ray system, an ultrasound system, and an MR imaging system.

10. The storage medium of claim 6, wherein the location subsystem is to arrange a review of the list of patients based on location information from the location device.

11. A method of implementing a location-based clinical information retrieval system, said method comprising:
   receiving, at a first computer processor implementing a location subsystem, a location information from a mobile location device including a second processor to be associated with and to be carried by a care provider to generate location information associated with the care provider;
   predicting, using the first computer processor, a predicted destination of the care provider based on the location information and one or more parameters associated with the mobile location device; and
   communicating, using the first computer processor, with an imaging workstation at the predicted destination to configure the imaging workstation based on the one or more parameters associated with the mobile location device, the one or more parameters including an identification of the care provider associated with the mobile location device,
   wherein configuring the imaging workstation includes:
      matching a patient at the predicted destination with the care provider based on a comparison of the predicted destination to a list of patients at or near the predicted destination for whom the care provider is eligible to provide care to identify the patient,
      retrieving the patient information for the patient, based on the identification of the patient and one or more patient services associated with the eligibility of the care provider to provide care for the patient, at the imaging workstation at the predicted destination in advance of the arrival of the mobile location device,
      wherein as the mobile location device is moved from one destination to another, different information packets are pre-loaded by the computer process and communicated to the imaging workstations at each destination.

12. The method of claim 11, further comprising providing the information packet to the mobile location device based on the predicted destination.

13. The method of claim 11, further comprising arranging a review of the list of patients based on a location information communicated from the mobile location device.

* * * * *